US005739422A

United States Patent [19]
Riviello et al.

[11] Patent Number: 5,739,422
[45] Date of Patent: Apr. 14, 1998

[54] MULTICYCLE LOOP INJECTION FOR TRACE ANALYSIS BY ION CHROMATOGRAPHY APPARATUS AND METHOD

[75] Inventors: John M. Riviello, Santa Cruz; Maria A. Rey, San Jose, both of Calif.

[73] Assignee: Dionex Corporation, Sunnyvale, Calif.

[21] Appl. No.: 574,643

[22] Filed: Dec. 19, 1995

[51] Int. Cl.⁶ .................................................. G01N 30/16
[52] U.S. Cl. ............................................................. 73/61.55
[58] Field of Search ................................. 73/61.52, 61.55, 73/61.56; 210/656, 659, 662; 422/70, 161

[56] References Cited

U.S. PATENT DOCUMENTS

| | | | |
|---|---|---|---|
| 3,975,946 | 8/1976 | Ball et al. | 73/61.56 |
| 4,102,179 | 7/1978 | Snell | 73/61.56 |
| 4,314,823 | 2/1982 | Rich, Jr. et al. | 23/230 |
| 4,699,718 | 10/1987 | Jones et al. | 73/61.52 X |
| 4,715,216 | 12/1987 | Muller | 73/61.1 |
| 4,775,476 | 10/1988 | Melcher et al. | 73/61.52 |
| 4,981,804 | 1/1991 | Hanaoka et al. | 73/61.52 X |
| 4,991,428 | 2/1991 | Heyde | 73/61.1 |
| 4,999,098 | 3/1991 | Pohl et al. | 204/301 |
| 5,042,293 | 8/1991 | Heyde | 73/61.1 |
| 5,248,426 | 9/1993 | Stillian et al. | 210/635 |
| 5,352,360 | 10/1994 | Stillian et al. | 210/198.2 |

OTHER PUBLICATIONS

Wetzel et al. "Determination of Trace Level Ions by Ion Chromatography with Concentrator Columns," Analytical Chemistry, 51(9):1532–1535 (Aug. 1979).

*Primary Examiner*—Michael Brock

[57] ABSTRACT

An ion chromatographic apparatus and method for on-column preconcentration of trace ionic contaminants for quantitative trace analysis by ion chromatography. The method includes the multi-cycle, sequential steps of loading and purging of sample solution into and out of a sample injection loop to cumulatively preconcentrate a separator column with a cumulative amount of sample. Each purging step includes directing pressurized liquid, at a substantially constant rate and for a predetermined period of time to the sample injection loop, to drive up to about 98% of the known volume of the sample solution from the sample injection loop. In turn, this flushed volume of sample solution passes through an ion exchange resin column for concentration of the trace ionic contaminants in the resin.

38 Claims, 5 Drawing Sheets

MULTICYCLE LOOP INJECTION FOR TRACE ANALYSIS BY ION CHROMATOGRAPHY APPARATUS AND METHOD

TECHNICAL FIELD

The present invention relates, generally, to ion chromatography, and more particularly, relates to trace analysis by ion chromatography.

BACKGROUND ART

The use of high purity water (HPW) is becoming increasingly important in a number of processes in the power and semiconductor industries. For example, in the power industries, HPW is employed as a coolant for the reactor and/or driving fluid for the steam turbine generators. Further, in the semiconductor industries, HPW is used in many manufacturing processes.

In either industry, the presence of trace ion contaminants in the high purity water indicates problems associated with system performance. In the power industries, the detection of trace ions in high purity water is employed to monitor ion intrusion into nuclear power plant secondary systems and corrosion. In the semiconductor industries, the presence of trace ion contaminants in the HPW can cause poor product yields, such as logic errors, heat dissipation problems and signal propagation problems with the semiconductor.

One method of detecting or measuring very low concentrations or trace anion and cation contaminants is through ion chromatography (IC). This technique has proved extremely useful and has been used in these industries for over fifteen years. Ion chromatography methods for the part per billion (ppb) and sub ppb determination of ions in high purity water have conventionally used concentrator columns. These columns contain a small volume of ion exchange resin with selectivity similar to the resin in the analytical or separation column.

Figure 1:
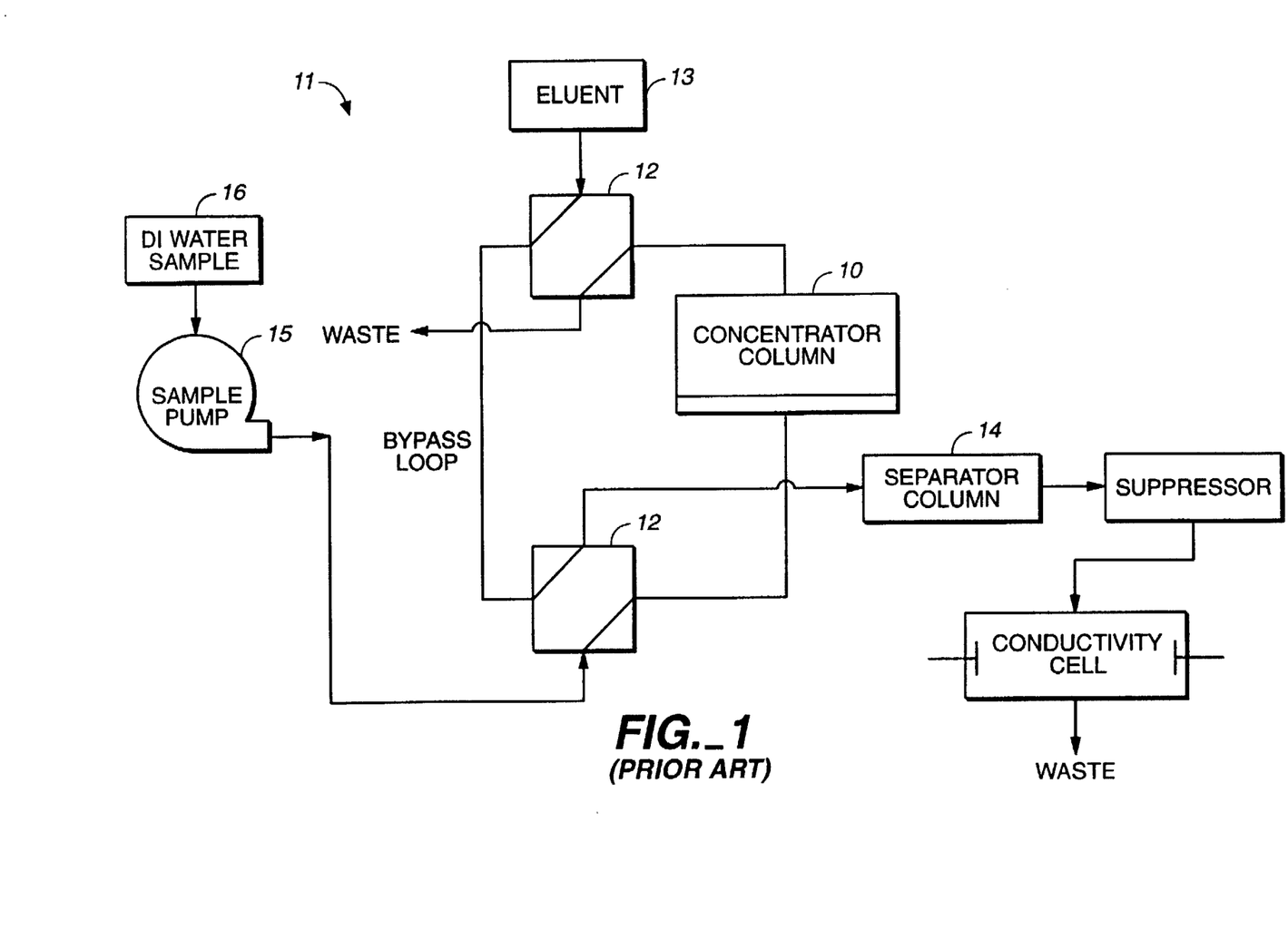
FIG. 1 is a schematic of a typical prior art ion chromatography column for trace analysis using preconcentration.

A known quantity of high purity water sample is pumped through concentrator column 10, as illustrated in typical prior art system configuration 11 of FIG. 1. The concentrator column retains anions or cations of interest from the HPW while allowing the remaining water matrix to pass through the column.

After the desired sample volume has been concentrated in the concentrator column 10, the concentrator column is switched in-line (via, valve 12) with the eluent from eluent source 13 and a separator column 14. The separation then proceeds by the normal elution process.

While this technique has proven useful for monitoring trace ionic contamination in HPW, several problems are inherent with this system. For example, eliminating pump flow rate perturbations when the concentrator column is switched into the eluent flow. Further, it is desirable that the sample pump 15, which transfers the sample solution from sample source 16 through concentrator column 10, provide a precise flow rate. Such precision enables accurate quantitation since a substantially known volume of sample will be passed through the concentrator.

Any residual sample solution from the pump 15, and hence, residual trace ionic contamination, will be added to the sample or standards which will significantly affect the results. Moreover, because the level of this contamination may be variable, this contamination cannot be removed or factored out as a fixed quantity. The employment of pumps with high precision, however, is very expensive, especially considering the fact that the eluent pumps also have high flow rate precision.

Another problem associated with conventional concentration sample pumps is in quantitation calibration. Quantitation calibration is normally performed by processing standards, which contain the ions of interest at known concentrations, through the concentrator column as described above. With proper calibration and sampling, this technique allows for the determination of trace ions down to the low ng/L (part-per-trillion) level.

Since external calibration is required, standards at the parts-per-trillion (PPT) level must be prepared. It is generally not practical to routinely produce accurate PPT level standards since the water used to dilute the more concentrated standards may contain trace ionic impurities at levels approaching the desired standard level.

Solutions to some of the problems associated with conventional IC methods used for trace ions in HPW have been addressed in the prior art. Typical of these patented inventions are disclosed in U.S. Pat. No. 4,715,216 to Mueller; and U.S. Pat. Nos. 4,991,428 and 5,042,293 to Heyde. Heyde describes an improved method for quantitation calibration at the PPT level which overcomes the problem of trace contamination from the water used to prepare standards at very low concentrations. Mueller on the other hand describes a technique which overcomes the problem caused by the drop in conductivity in the beginning of a chromatogram when a concentrator column is used.

While these prior art assemblies have improved the performance of ion chromatography for the analysis of high purity water, the above-mentioned problems related to the use of a sample pump for concentration still exist.

As an alternative to conventional concentration, on-column preconcentration may be employed as a means for eliminating the need for a sample pump. In this technique, a large sample loop, which may have a volume as large as 10 mL (for a 4 mm diameter column), is switched in-line or in fluid communication with the separator column and an eluent source for direct loading of the sample on the column by the eluent.

Accordingly, mixing of the sample solution with the pumped eluent employed to sweep the sample solution into the separator column must be minimized during the column loading to avoid degrading the separation of the early eluting components. Another problem associated with on-column preconcentration is that while it is desirable to employ a large volume sample loop, the physical dimension of the loop may be limiting for performance purposes. For example, a large volume sample loop having a relatively large inner diameter passage and a short length tends to be problematic when subjected to the relatively higher pressures provided by the eluent pump (i.e., 1000–3000 psi). As a result, the tubing should have an internal diameter so that the volume will be significant, but the length, and hence pressure drop through the tubing, minimized. The wall thickness of the tubing must allow for the high pressure requirements.

In contrast, tubing with a smaller interior diameter will require an injection loop of greater length to provide the proper sample volume. This arrangement may be problematic in that the increased passage length of the injection loop fosters susceptibility to bubble formation and retention. These bubbles substantially reduce volume reproducibility which adversely affect analytical performance problems.

DISCLOSURE OF INVENTION

Accordingly, it is an object of the present invention to provide an apparatus and method for chromatographic separation and quantitative analysis of ionic species in a sample solution.

Another object of the present invention is to simplify ion chromatographic trace analysis of anions and cations in high purity water.

Still another object of the present invention is to provide an ion chromatographic separation apparatus and method which enables on-column preconcentration of a large predetermined volume of sample solution free of contamination or degradation from the eluent.

Yet another object of the present invention is to provide an ion chromatographic separation apparatus and method enabling quantitation calibration which minimizes error caused by contamination and by dilution.

It is a further object of the present invention to provide an ion chromatographic separation apparatus and method which is durable, compact, easy to maintain, has a minimum number of components, and is easy to use by unskilled personnel.

In accordance with the foregoing objects, the present invention provides a method of on-column preconcentration of trace ionic contaminants for quantitative trace analysis by ion chromatography. The method includes the steps of: (A) loading sample solution, having trace ionic species, into a sample injection loop of a known volume to substantially fill the loop with the sample solution and to remove any non-sample solutions therefrom. Thereafter, (B) directing pressurized liquid, at a substantially constant rate and for a predetermined period of time, to and through the sample injection loop to drive up to about 98% of the known volume of the sample solution from the sample injection loop through an ion exchange resin column for concentration of the trace ionic contaminants onto the resin. This resin retains the trace ion contaminants therein and permits passage of the remaining solution therethrough. The method of the present invention further includes the step of (C) repeating steps A and B, sequentially, until a total predetermined volume of sample solution has passed through the resin column; and (D) passing eluent through the ion exchange resin column to separate predetermined ionic contaminants of interest from the resin column.

The method of the present invention is best achieved on a chromatographic separation apparatus which includes an eluent source providing pressurized eluent, and a sample source of the sample solution having an input port and a waste port. The present invention further includes a sample injection loop having a sample inlet and a sample outlet to enable loading the sample solution in the loop. The injection loop is of a known volume in the range of about 100 µL to about 8 mL which includes a predetermined inner diameter in the range of about 0.5 mm to about 3 mm. A separator column, is included, as well as an injection valve assembly having a first valve portion in selective fluid communication with the eluent source, the sample inlet and the sample input port, and a second valve portion in selective fluid communication with the sample waste port, the sample outlet and the separator column.

The first valve portion is selectively movable between a loop loading position and a column loading position. In the loop loading position, the first valve portion couples the sample inlet with the sample input port to load the injection loop with the sample solution, while in the column loading position, the valve couples the eluent source with the sample inlet to move a fraction of the known volume sample solution from the loop toward the second valve portion. Regarding the second valve portion, it is selectively movable between a loop loading condition and a column loading condition. In the loop loading condition, the second valve portion couples the sample outlet with the sample waste port to load the injection loop with the sample solution when the first valve portion is in the loop loading position. In contrast, in the column loading condition, the second valve portion couples the sample outlet with the separator column to move the fraction of the known volume of sample solution from the loop and the second valve portion to the separator column when the first valve portion is in the column loading position.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

DETAILED DESCRIPTION OF THE INVENTION

While the present invention will be described with reference to a specific embodiment, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
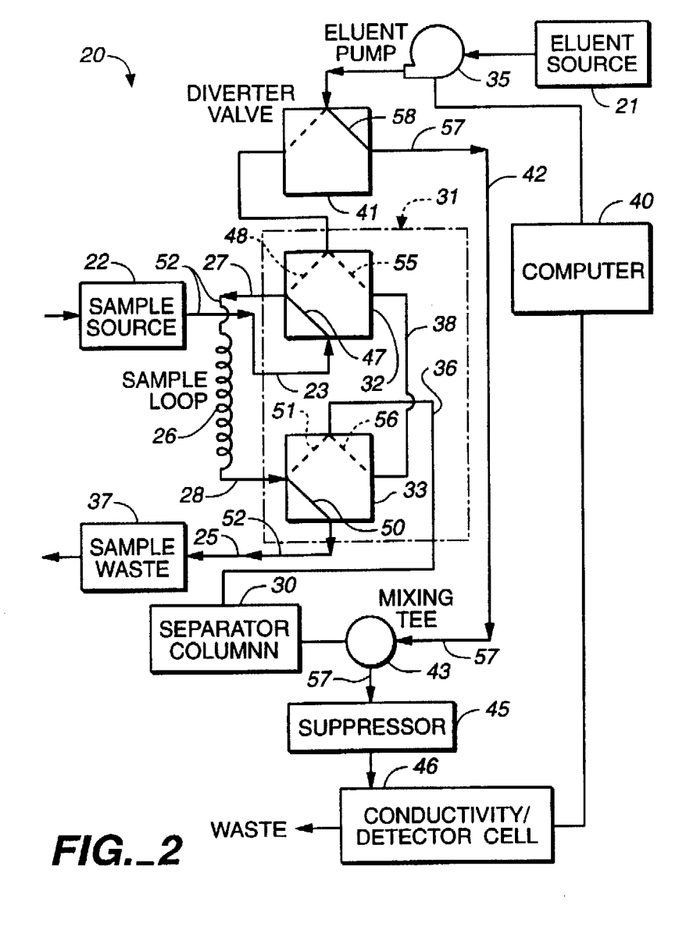
FIG. 2 is a schematic of a multiple-cycle loop ion chromatography apparatus for trace analysis constructed in accordance with the present invention, and illustrating loading of sample solution in a sample injection loop.

Attention is now directed to FIG. 2 where an apparatus, generally designated 20, for chromatographic separation and quantitative analysis of ionic species in a sample solution is illustrated. Chromatographic separation apparatus 20 includes an eluent source 21 providing pressurized eluent at a substantially constant flow rate, and a sample source 22 of the sample solution having an input port 23 and a waste port 25. A sample injection loop, generally designated 26, is included having a sample inlet 27 and a sample outlet 28 to enable loading the sample solution in loop 26. The injection loop has a known volume in the range of about 100 µL to about 8 mL. This is specifically accomplished by tubing having a predetermined inner diameter in the range of about 0.5 mm to about 3 mm, the reasons of which will be described in greater detail below. Further, the present invention includes a separator column 30 having ion exchange resin capable of preconcentration of the trace ionic contaminants therein, and an injection valve assembly, generally designated 31, having a first valve portion 32 and a second valve portion 33. First valve portion 32 is in selective fluid communication with eluent source 21, sample inlet 27 and sample input port 23, while second valve portion 33 is in selective fluid communication with sample waste port 25, sample outlet 28 and separator column 30.

Figure 3:
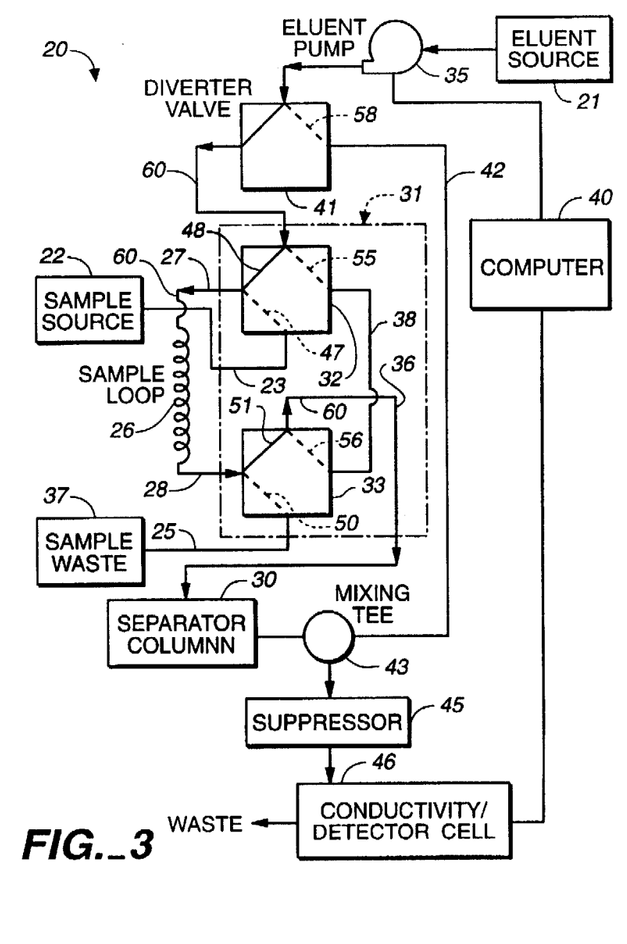
FIG. 3 is a schematic of the multiple-cycle loop ion chromatography apparatus of FIG. 2 illustrating flushing of the sample solution the injection loop to the separator column.

Injection valve assembly 31 controls first and second valve portions 32, 33 to load sample injection loop 26 completely with sample solution from sample source 22, while removing any non-sample solutions therefrom (FIG. 2). Subsequently, injection valve assembly 31 closes fluid communication between the sample source and the injection loop, and opens fluid communication between the high precision eluent pump 35 and the sample loop 26 (FIG. 3). This urges the pumped eluent into contact with the sample solution contained in the injection loop to sweep the sample solution through the separator column 30.

In accordance with the present invention, by precisely controlling the flow rate and operation time of the high precision eluent pump, a precise volume of eluent can be delivered through the system. In turn, the precise volume of eluent delivered to the injection loop displaces an equivalent volume of sample solution from the injection loop. Hence, a precise, calculated volume of sample solution will be subsequently passed through separator column 30.

Moreover, this assembly eliminates the need for an independent sample pump as a means to drive the sample solution through the resin column for on-column preconcentration since the more precise eluent pump 35, in combination with injection valve assembly 31, is employed. Manufacturing costs are therefore decreased, as well as reducing maintenance costs. The present invention further eliminates the need for a separate concentration column since the separator column is suitable for both a concentration column and a separator column.

The present invention on-column preconcentration, however, is initially limited to an amount of sample solution no greater than the known volume provided by injection loop 26. This presents a substantial problem since the known volume of the sample injection loop of the present invention is relatively small (i.e., about 100 µL to about 2 mL for a 2 mm separator column, and about 400 µL to about 8 mL for a 4 mm separator column) due to the relatively small inner diameter tube (i.e., about 0.5 to about 1 mm for a 2 mm separator column, and about 1 mm to about 3 mm for a 4 mm separator column). As above-indicated, this dimensional configuration is desirable to reduce potential rupture of the sample loop when subjected to the substantially higher pressures provided by the eluent pump and the separator column. Moreover, the reduced tube length of the injection loop increases analytical performance by increasing volume reproducibility and reliability due to less bubble retention.

The drawback to this configuration, however, is that the resulting small volume of sample solution provided by the injection loop is an amount insufficient to perform on-column preconcentration for trace analysis. The prior art on-column preconcentration assemblies could merely replace the injection loops with larger volume sample injection loops which often resulted in the above-mentioned analytical problems or the like. In contrast, the present invention employs a multi-cycle on-column preconcentration loading technique to cumulatively pass through the resin column the proper quantity of sample solution.

Therefore, as will be described in greater detail below, several cycles of loading the injection loop with sample (FIG. 2), sweeping the sample therein to the resin column by the eluent pump (FIG. 3), and then loading the sample injection loop again are required.

One problem associated with multi-cycle loading for on-column preconcentration, however, is passing or sweeping through the injection loop a volume of eluent greater than the known volume of sample solution retained in the injection loop. In this event, some of the eluent may inadvertently pass through injection loop 26 into a connecting conduit 36 (FIG. 3), and prematurely through the ion exchange resin column 30 causing chromatographic elution. Hence, certain ions captured in the ion exchange resin may be prematurely released or separated from the column which results in degradation of the chromatographic separation and comprises quantitation.

To eliminate eluent from passing through resin column 30 during fluid communication between the eluent source and the injection loop (FIG. 3), in accordance with the present invention, less than 100% of the known volume of the injection loop will be displaced in one cycle. In the preferred form, up to about 98% may be displaced, and more preferably, 5% to about 95% will be displaced for loading of the resin column. This technique assures that eluent will not be prematurely passed into connecting conduit 36, and on through the resin column to cause inadvertent ion separation from the resin during the sample solution loading sequence. Subsequently, injection valve assembly 31 is selectively configured to close fluid communication of sample injection loop 26 with resin column 30 and eluent source 21; and reopen fluid communication of the injection loop with sample solution source 22 and sample waste 37. As above-mentioned, this procedure loads or fills injection loop with the known volume of sample solution while simultaneously removing any non-sample solutions, such as eluent, from the injection loop.

By employing the high precision eluent pump, the quantity or volume of sample solution delivered is highly reproducible. Accordingly, the present invention is particularly suitable for the multi-cycle on-column preconcentration technique. By sequentially repeating or cycling this procedure over and over, an accurate cumulative volume of sample solution can be passed through the resin column for concentration of the trace ions thereon. That is, the trace ions from each calculated portion (i.e., up to 98% of the known volume) of sample solution will concentrate on the resin column. In this manner, resin column 30 is further employed as a concentration column. This system also operates with a guard column placed between injection valve 31 and separator column 30.

For example, for an on-column preconcentration requiring about 20 mL of sample solution to perform trace analysis, and a system employing a sample loop having a known volume of about 1 mL, at about 80% displacement of the known volume of injection loop, at least 25 cycles would be required to pass a cumulative volume of 20 ml of sample solution through resin column.

Figure 4:
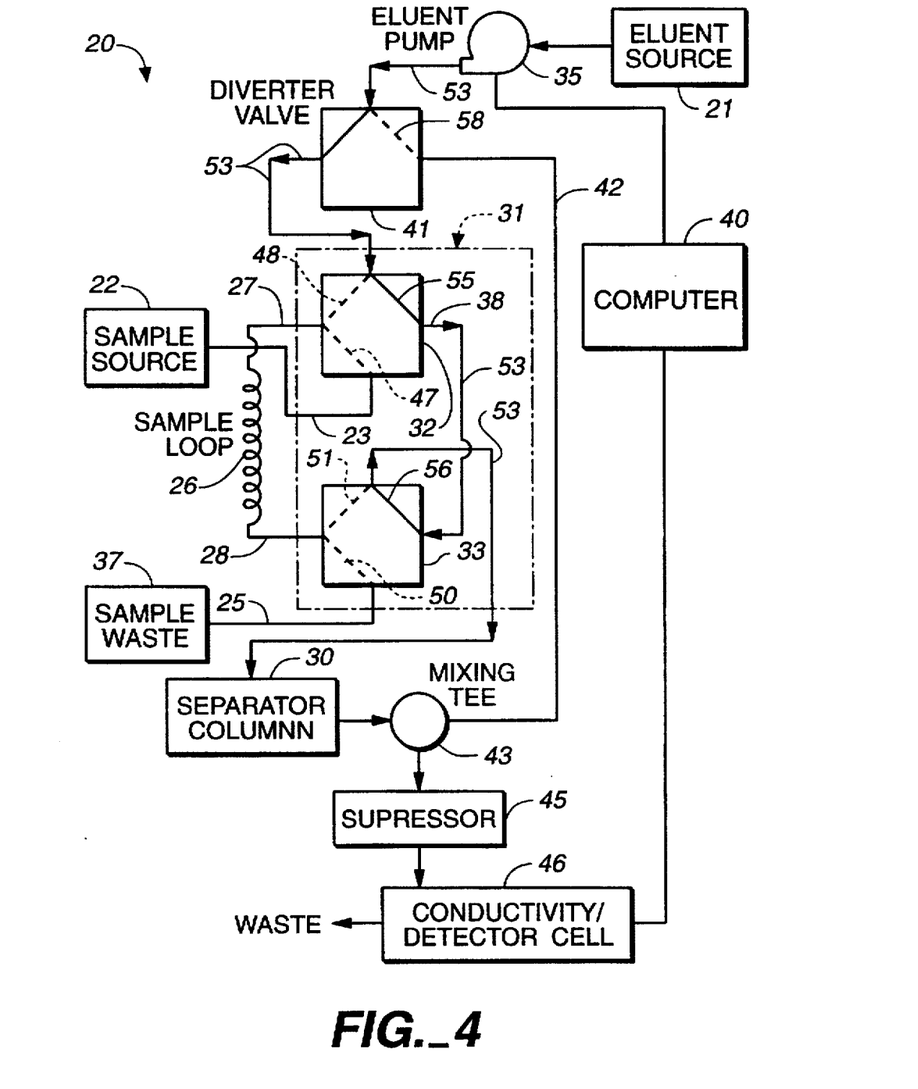
FIG. 4 is a schematic of the multiple-cycle loop ion chromatography apparatus of FIG. 2 illustrating separation of selected ions concentrated on the separator column.

Subsequently, as schematically illustrated in FIG. 4, injection valve assembly 31 can be configured to enable eluent to pass through resin column 30 for elution of the particular anion and cation species from the ion exchange resin. This elution procedure, as well as the ion exchange resins employed, are well known in the field and are described in greater detail in U.S. Pat. No. 4,314,823, incorporated at this point by reference.

Turning back to FIG. 2, the present invention will be described in detail. Briefly, sample injection loop 26 is preferably provided by flexible inert tubing such as TEFLON®, tefzel or Polyether-ether ketone (PEEK). Opposite ends (i.e., sample inlet 27 and sample outlet 28) of loop 26 are coupled to injection valve assembly 31 to control fluid communication thereof with eluent source 21/resin column 30, and with sample source 22/sample waste 37.

Injection valve assembly 31 includes first valve portion 32, selectively fluid communicating sample inlet 27 with either eluent source 21 or the sample input port 23 of sample source 22. Further, valve portion assembly 31 includes second valve portion 33, selectively fluid communicating sample outlet 28 with either sample waste port 25 or the resin/separator column 30.

First valve portion 32 is selectively movable between a loop loading position (FIG. 2) and a column loading position (FIG. 3). In the loop loading position, first valve portion 32 fluid couples sample inlet 27 with sample input port 23 (as illustrated by solid line 47 in FIG. 2) to enable loading of injection loop 26 with the sample solution. In contrast, in the column loading position, first valve portion 32 couples eluent source 21 with sample inlet 27 (solid line 48 in FIG. 3) to displace up to about 98% of the known volume sample solution from injection loop 26 toward the second valve portion.

In a similar manner, second valve portion 33 is selectively movable between a loop loading condition (FIG. 2) and a column loading condition (FIG. 3). In the loop loading condition, second valve portion 33 fluid couples sample outlet 28 with the sample waste port 25 (as illustrated by solid line 50 in FIG. 2) to load injection loop 26 with the sample solution when first valve portion 32 is in the loop loading position. In contrast, in the column loading condition, second valve portion 33 fluid couples sample outlet 28 with separator column 30 (solid line 51 in FIG. 3) to enable sample solution flow from injection loop 26 and second valve portion 33 to separator column 30 when the first valve portion is in the column loading position.

Accordingly, when both the first valve portion 32 is in the loop loading position and the second valve portion 33 is in the loop loading condition, sample source will urge new sample solution into injection loop 26 (as shown by arrows 52 in FIG. 2). Consequently, non-sample solution resident in sample injection loop 26 will be removed therefrom and urged toward sample waste port 25 during loading.

Depending upon the sample flow rate, which is proportional to the sample supply pressure (typically between about 10 psi to about 100 psi) and the known volume of injection loop 26, the time required to load the sample injection loop may vary between about 10 seconds to about 300 seconds. As mentioned, this loading technique is performed without a sample pump.

In accordance with the present invention, injection valve assembly 31 further includes a bypass tube 38 selectively fluid coupling eluent source 21 with separator column 30 in a manner bypassing injection loop 26 to enable chromatographic separation. This configuration is employed after the on-column preconcentration has been completed, and ion chromatographic separation is about to commence.

As shown in FIG. 4, bypass tube 38 is coupled between first valve portion 32 and second valve portion 33 for direct fluid communication therebetween. Arrows 53 illustrate that eluent source 21 is placed in direct fluid communication with separator column 30 for trace analysis such that the eluent flows directly through both first valve portion 32 and second valve portion 33 to connecting conduit 36. Hence, first valve portion 32 is further selectively movable to a bypass position, providing fluid communication between eluent source 21 with second valve portion 33 (as illustrated by solid line 55 in FIG. 4), while first valve portion 32 is out of the column loading position. Similarly, second valve portion 33 is further selectively movable to a bypass condition, providing direct fluid communication between first valve portion 32 and separator column 30 (solid line 56 in FIG. 4), to enable passage of eluent through separator column 30 for chromatographic separation. It will be understood that in this configuration, second valve portion 33 is out of column loading condition and first valve portion 32 is in the bypass position.

First valve portion 32 and second valve portion 33 are preferably provided by conventional valves commonly employed in the ion chromatographic and the HPLC fields. Hence, the valves may be mechanically or pneumatically actuated with an actuation device such as computer 40. Further, eluent pump 35 is preferably provided by a dual piston pump having superior flow properties such as those provided by high precision IC or HPLC pumps. In the preferred embodiment, the flow rate is between 0.1 to 2.0 mL/min. These pumps, of course, must be capable of substantial precision to maintain a substantially constant flow rate for predetermined periods of time.

A diverter valve 41 may be provided upstream from injection valve assembly 31 which can redirect eluent flow through a bypass conduit 42 coupling eluent source 21 directly to a mixing tee 43, bypassing injection valve assembly 31. This valve is employed to bypass the injection valve assembly 31, sample injection loop 26 and separator column 30 while first valve portion 32 and second valve portion 33 are deployed in the loop loading position and the loop loading condition, respectively (FIG. 2). In this configuration, as shown by arrows 57, eluent is assured to flow continuously through suppressor 45 and detector 46 which is imperative to maintain detector stability.

Separator column 30 is provided by a high performance ion chromatography column capable of separating the analytes (contaminants) of interest. Typical of these columns is the DIONEX CS12A (2 mm) chromatographic separator. Further, suppressor 45 is employed to enhance detection when a flow through conductivity detector is used. Typical of these suppressors are disclosed in U.S. Pat. Nos.: 4,999,098; 5,248,426; and 5,352,360, herein incorporated by reference. Other detectors, however, such as electrochemical or photometric could be employed in this invention with or without a suppressor.

The computer 40 is capable of acquiring output from the detector and also can be used to control the chromatographic system. Hence, the microprocessor or computer 40 can be employed to actuate diverter valve 41 and injection valve assembly 31 at any time during the analysis.

In addition, this embodiment allows for quantitation calibration using a similar scheme. In this case, the specified volume of standard delivered is between 5 and 95% of the injection loop volume. Typically, only one loading cycle is used for calibration although the calibration scheme may involve loading at different volumes or standards at different concentrations. This process allows for quantitation calibration to be performed using standards with concentrations significantly higher than the samples to be analyzed.

This procedure minimizes the error caused by having to prepare standards at lower concentrations which may be contaminated by the water used for dilution.

For example, suppose one wishes to determine the ionic contamination in HPW at the 1 µg/L(ppb) level. Using the present invention would require loading approximately 5 mL of sample to achieve the required detection limits. A typical sample loop volume is 1.3 mL. Typically, a standard curve would be established from 0.1–10.0 µg/L. This would normally require preparing standards at the 0.1, 1.0 and 10.0 µg/L levels. As mentioned, accurate preparation and storage of low level standards is difficult due to contamination and stability of the standards. Suppose that for standardization, a 10.0 µg/L standard was prepared. With proper care, an accurate 10.0 µg/L standard can be prepared without contamination. The first calibration point (0.1 µg/L) would be generated by allowing only 50 µL of the standard to load to the separator column. The 1.0 µg/L calibration would be accomplished by allowing 500 µL of the 10.0 µg/L standard to load to the concentrator column. Finally, the 10.0 µg/L calibration would be accomplished by allowing 5.0 mL of the 10 µg/L standard to load to the separator.

SEQUENCE OF OPERATION

The following description will refer to one sequence of operation of the system of FIGS. 2–4. For simplicity of description, flow of solutions will be described in order of flow without reference to valve settings. The valves will be assumed to allow flow in the described manner.

In the first step, sample injection loop 26 is loaded with sample solution, having trace ionic contaminants, substantially filling loop 26 therewith and removing any non-sample solutions therefrom. This is accomplished first moving diverter valve 41 to a bypass position (shown by solid line 58 in FIG. 2) which directs eluent from eluent source 21 and eluent pump through mixing tee 43 and onto suppressor 45. As mentioned, this assures fluid flow through the suppressor to maintain stability, as illustrated by arrows 57.

Simultaneously, first valve portion 32 and second valve portion 33 are switched to the loop loading position (as illustrated by solid line 47 in FIG. 2) and the loop loading condition (solid line 50), respectively. Sample solution will then flow (as illustrated by arrows 52) through injection loop 26 while simultaneously removing any resident eluent or the like to sample waste 37. Depending upon the capacity or volume of the sample injection loop and the flow rate of the sample solution, the time required to load the loop may vary from 10–300 seconds.

After completion of filling injection loop 26, first valve portion 32 and second valve portion 33 are switched to the column loading position (as illustrated by solid line 48 in FIG. 3) and the column loading condition (solid line 51), respectively. Hence, eluent pump directs pressurized eluent, at a substantially constant rate and for a predetermined period of time to sample injection loop 26, as illustrated by arrows 60. Moreover, up to about 98% of the known volume of the sample solution is displaced by eluent so that an equivalent amount passes through connecting conduit 36 and through ion exchange resin column 30.

This is most preferably controlled by the actuation of diverter valve 41 for a predetermined period of time to enable fluid communication between eluent source 21 and injection valve assembly 31. For example if a sample injection loop of 1.0 mL was used and the eluent flow rate from eluent pump 35 was 0.2 mL/minutes, and the system was configured to load 80% (0.8 mL) of the contents or known volume of injection loop 26, diverter valve 41 would direct eluent through valve assembly 31, and hence, to injection loop 26 for 4 minutes (0.8 mL/0.2 mL/min.).

Subsequently, diverter valve 41 will be switched to the bypass position (as illustrated by solid line 58 in FIG. 2) to direct eluent flow from injection valve assembly 31 back to mixing tee 43 and onto the suppressor 45 and cell/detector 46. This assures that there is always flow through the suppressor detector which is important in maintaining detector stability.

In accordance with the present invention, the above mentioned steps are repeated sequentially until the predetermined total or cumulative volume of sample solution has passed through separator column 30 for on-column preconcentration for trace analysis. Hence, this method of sample loading enables a precise, large volume of sample to be loaded to the separator column without eluent passing through the column. If eluent passes to the separator after sampling loading, chromatographic elution will begin which is undesirable at this stage of the analysis.

The next step includes switching first valve portion 32 and second valve portion 33 to the bypass position (as illustrated by solid line 55 in FIG. 4) and the bypass condition (solid line 56), respectively. In this configuration the eluent is passed through the ion exchange resin column, as represented by arrows 53, to cause chromatographic elution.

In the alternative, during the last pass, the entire injection loop volume maybe loaded onto separator column 30, and the chromatographic elution process may begin as the eluent reaches the separator column.

EXAMPLE 1

A Dionex DX500 chromatograph was configured as shown in FIG. 2. Chromatography separations of inorganic cations was accomplished using a Dionex CS12A (2 mm) separator and detection used a Dionex CSRS-2 mm suppressor. The injection loop size was 1300 µL of which approximately 77% (1000 µL) was loaded on to the separator. The test sample consisted of 18.2MΩ-cm deionized water to which was added the following test analytes at µg/L (ppb) concentrations:

lithium—0.38 µg/L, sodium—1.5 µg/L, ammonium—1.9 µg/L, potassium—3.8 µg/L, magnesium—1.9 µg/L, and calcium—3.8 µg/L.

Figure 5A:
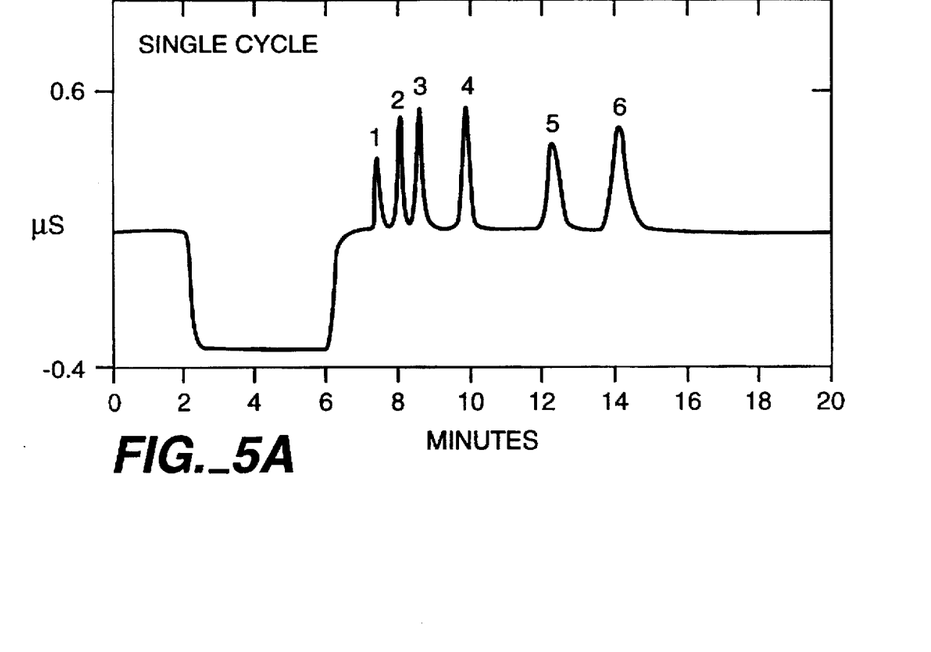
FIG. 5 is a chromatogram of analyzed sample solution comparing a single cycle and a five cycle employing the present invention.
Figure 5B:
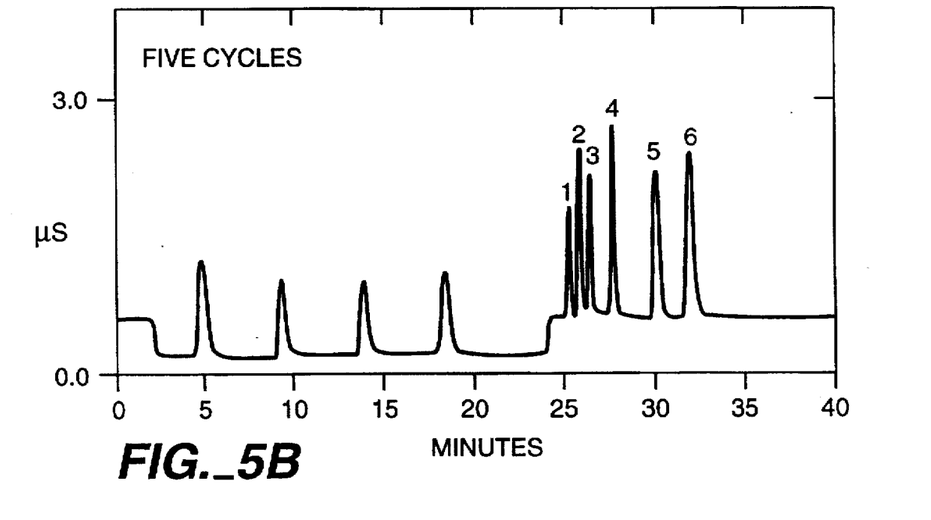

The timed events program used controlled sample loading. FIG. 5 is a chromatogram obtained using a single and five-cycle sample loading. Note that no chromatographic degradation is observed and, as expected, the peak response is increased approximately five fold for the five-cycle experiment. In order to demonstrate the linearity and precision of the multi-cycle sample loading technique, the data obtained for peak area of each of the components was plotted against the cumulative number of passes (1–5). If each pass resulted in the same volume, the relationship should be linear. Table I shows detection limits and examination of the data shows that the concentration for each analyte in the five pass chromatogram is about one-fifth that of the single pass. This is consistent with precise sampling loading volumes during each pass.

Figure 6:
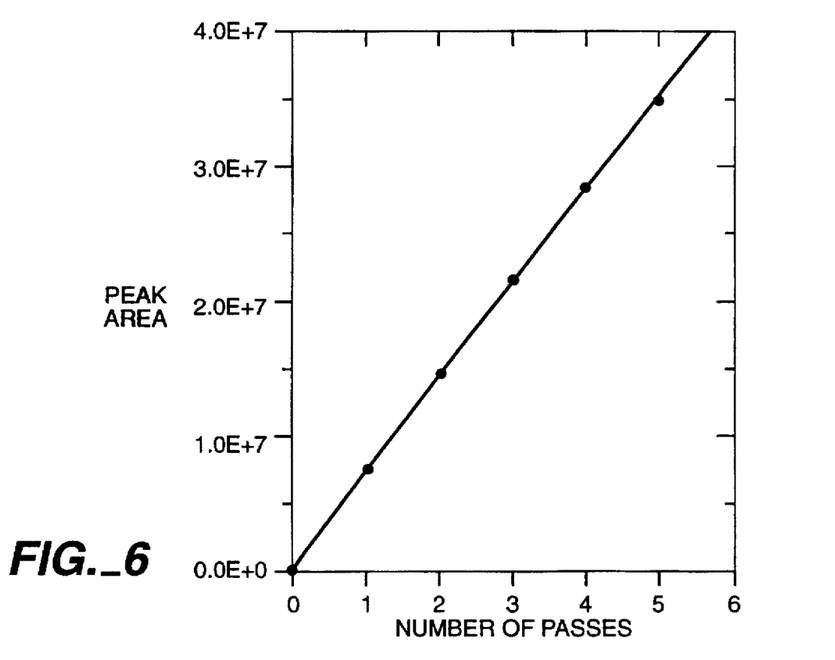
FIG. 6 is a graph illustrating the Potassium Peak Area versus the number of injection loading cycles.
Figure 7:
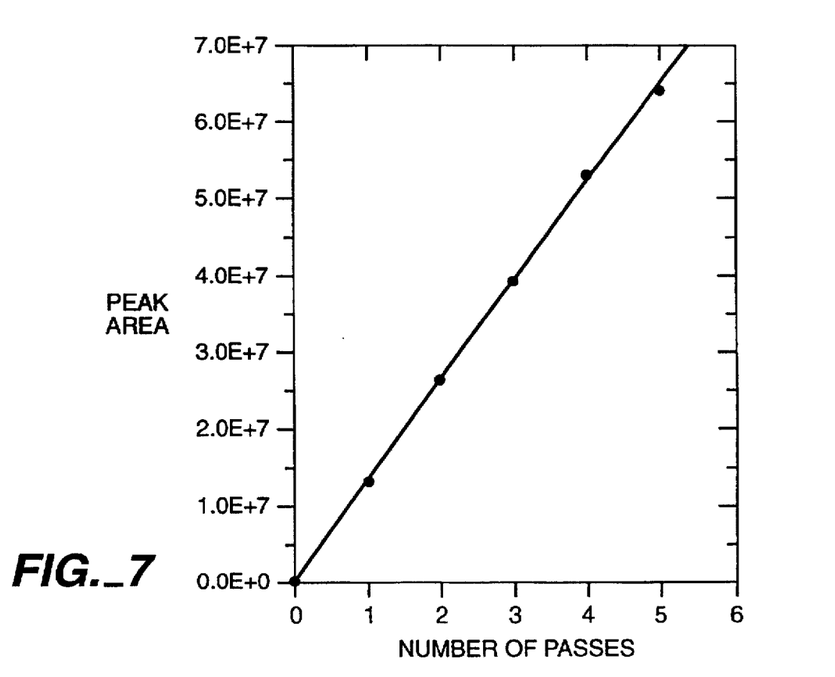
FIG. 7 is a graph illustrating the Calcium Peak Area versus the number of injection loading cycles.

Moreover, FIG. 6 shows the results obtained for potassium, while FIG. 7 illustrates the results for calcium. As can be seen from these results, the precision of multi-cycle sample loading is extremely good.

TABLE 1

| Analyte | (Analyte Concentration (µg/L.)) | |
|---|---|---|
| | Single Pass | Quintuple Pass |
| Lithium | 0.0061 | 0.0013 |
| Sodium | 0.016 | 0.0032 |
| Ammonium | 0.018 | 0.0049 |
| Potassium | 0.035 | 0.0072 |
| Magnesium | 0.025 | 0.0047 |
| Calcium | 0.044 | 0.0084 |

While the present invention is most suitable for use in ion chromatography, it will be appreciated that the present invention may be employed in High Performance Liquid Chromatography (HPLC) as well. In this embodiment, the separator column would be replaced by a normal or reverse phase column. Further, those skilled in the art would recognize that the analogous eluents employed in HPLC would replace those employed in ion chromatography.

What is claimed is:

1. An apparatus for chromatographic separation and quantitative analysis of ionic species in a sample solution comprising:

an eluent source providing pressurized eluent at a substantially constant rate;

a sample source of said sample solution having an input port and a waste port;

a sample injection loop having a sample inlet and a sample outlet to enable loading said sample solution in said loop, said loop having a known volume in the range of about 100 µL to about 8 mL, a predetermined inner diameter in the range of about 0.5 mm to about 3.0 mm;

a separator column having ion exchange resin capable of concentration of said trace ionic contaminants therein; and an injection valve assembly having a first valve portion in selective fluid communication with said eluent source, said sample inlet and said sample input port, and having a second valve portion in selective fluid communication with said sample waste port, said sample outlet and said separator column, said first valve portion and said second valve portion being adapted to cooperate therebetween to load said sample injection loop with sample solution from said sample source, and cooperate to flush up to about 98% of the known volume of sample solution from the sample injection loop, with eluent from said eluent source, and through said separator column without passing any eluent through said separator column during the flush.

2. The apparatus as defined in claim 1 wherein, said first valve portion being selectively movable between a loop loading position, coupling said sample inlet with said sample input port to load said injection loop with said sample solution, and a column loading position, coupling said eluent source with said sample inlet to move a fraction of said known volume of sample solution from said loop toward said second valve portion; and said second valve portion being selectively movable between a loop loading condition, coupling said sample outlet with said sample waste port to load said injection loop with said sample solution when said first valve portion is in said loop loading position, and a column loading condition, coupling said sample outlet with said separator column to move said fraction of said known volume of sample solution from said loop and said second valve portion to said separator column when said first valve portion is in said column loading position.

3. The apparatus as defined in claim 2 further including:

a bypass tube selectively coupling said eluent source with said separator column in a manner bypassing said injection loop to enable chromatographic separation.

4. The apparatus as defined in claim 3 wherein, said bypass tube is coupled between said first valve portion and said second valve portion, said first valve portion further selectively movable to a bypass position fluid communicating said eluent from said eluent source with said second valve portion while said first valve portion is out of said column loading position, and said second valve portion further selectively movable to a bypass condition fluid communicating said eluent from said eluent source with said separator column while said second valve portion is out of said column loading condition and said first valve portion is in said bypass position.

5. The apparatus as defined in claim 2 wherein, said known volume of said injection loop is about 100 µL to about 2 mL for a 2 mm separator, and about 400 µL to about 8 mL for a 4 mm separator.

6. The apparatus as defined in claim 5 wherein, the inner diameter of said injection loop is about 0.5 mm to about 1 mm for a 2 mm separator, and about 1 mm to about 3 mm for a 4 mm separator.

7. The apparatus as defined in claim 2 wherein, said eluent source includes a high precision eluent pump assembly delivering eluent to said sample injection loop at a substantially constant rate.

8. A method of on-column preconcentration of trace ionic contaminants for quantitative trace analysis by ion chromatography comprising the steps of:

(A) loading sample solution, having trace ionic contaminants, into a sample injection loop of a known volume substantially filling said loop with said sample solution and removing any non-sample solutions therefrom;

(B) thereafter, directing pressurized liquid, at a substantially constant rate and for a predetermined period of time, to said sample injection loop to drive up to about 98% of the known volume of said sample solution from said sample injection loop through an ion exchange resin column for concentration of said trace ionic contaminants onto said resin column, retaining trace ion contaminants and permitting passage of the remaining solution;

(C) repeating steps A and B, sequentially, until a total predetermined volume of sample solution has passed through said resin column; and (D) passing eluent through said ion exchange resin column to separate predetermined ionic contaminants of interest from said resin column.

9. The method as defined in claim 8 wherein, said loading step (A) includes the step of (E) providing fluid coupling of sample solution from a sample source with a sample inlet into said injection loop to enable flow said sample solution therethrough and into said injection loop.

10. The method as defined in claim 9 wherein,
said loading step (A) further includes the step of (F) blocking fluid coupling of said liquid with said sample inlet to preclude flow of said liquid therethrough and into said injection loop.

11. The method as defined in claim 10 wherein,
said providing step (E) and said blocking step (F) are accomplished by an injection valve assembly having a first valve portion in selective fluid communication with said eluent source, said sample inlet of injection loop and a sample input port of said sample source, said first valve portion being movable from a column loading position to a loop loading position, fluid coupling said sample inlet with said sample input port while disconnecting fluid coupling of said liquid through said sample inlet.

12. The method as defined in claim 11 wherein,
said loading step (A) is further accomplished by a second valve portion of said injection valve assembly in selective fluid communication with a sample waste port of said sample source, a sample outlet of said injection loop and said resin column, said second valve portion being selectively movable from a column loading condition to a loop loading condition, fluid coupling said sample outlet with said sample waste port while disconnecting fluid coupling of said sample outlet with said resin column, when said first valve portion is in said loop loading position.

13. The method as defined in claim 12 wherein,
said directing step (B) includes the step of (G) providing fluid coupling of said liquid from a liquid source with said sample inlet into said injection loop to enable flow of said liquid therethrough and into said injection loop.

14. The method as defined in claim 13 wherein,
said directing step (B) further includes the step of (H) blocking fluid coupling of said sample solution from said sample source with said sample inlet to preclude flow of said sample solution therethrough and into said injection loop.

15. The method as defined in claim 14 wherein,
said providing step (G) and said blocking step (H) are accomplished by movement of said first valve portion from said loop loading position to said column loading position, fluid coupling said liquid source with said sample inlet while disconnecting fluid coupling of said sample source from said sample inlet.

16. The method as defined in claim 15 wherein,
said directing step (B) is further accomplished by movement of said second valve portion from said loop loading condition to said column loading condition, fluid coupling said sample outlet with said resin column for passage of said known volume of sample solution therethrough, while disconnecting fluid coupling of said sample outlet with said waste port.

17. The method as defined in claim 13 wherein,
said passing step (D) is accomplished by providing a bypass tube selectively fluid coupling an eluent source with said resin column in a manner bypassing said injection loop to enable chromatographic separation.

18. The method as defined in claim 17 wherein
said bypass tube is coupled between said first valve portion and said second valve portion,
said first valve portion further selectively movable to a bypass position fluid communicating said eluent source with said second valve portion while said first valve portion is out of said column loading position, and said second valve portion further selectively movable to a bypass condition fluid communicating said eluent from said eluent source with said separator column while said second valve portion is out of said column loading condition and said first valve portion is in said bypass position.

19. The method as defined in claim 8 wherein,
said directing step (B) includes the step of (G) providing fluid coupling of said liquid from a liquid source with a sample inlet into said injection loop to enable flow said liquid therethrough and into said injection loop.

20. The method as defined in claim 19 wherein,
said directing step (B) further includes the step of (H) blocking fluid coupling of said sample solution from a sample source with said sample inlet to preclude flow of said sample solution therethrough and into said injection loop.

21. The method as defined in claim 8 wherein,
said liquid is provided by eluent.

22. The method as defined in claim 8 wherein,
said resin column is provided by a separator column.

23. The method as defined in claim 8 wherein,
about 5% to about 95% of said known volume of sample solution in said injection loop is passed through said resin column during said directing step (B).

24. The method as defined in claim 8 wherein,
the known volume of said sample injection loop is in the range of about 100 µL to about 8 mL, including a predetermined inner diameter in the range of about 0.5 mm to about 3 mm.

25. The method as defined in claim 8 wherein,
said passing step (D) is accomplished by providing a bypass tube selectively fluid coupling an eluent source with said resin column in a manner bypassing said injection loop to enable chromatographic separation.

26. An apparatus for chromatographic separation and quantitative analysis of ionic species in a sample solution comprising:
an eluent source providing pressurized eluent at a substantially constant rate;
a sample source for sample solution having an input port and a waste port;
a sample retaining device of known volume having a sample inlet and a sample outlet to enable loading said sample solution in said retaining device,
a separator column; and
an injection assembly having a first communication portion in selective fluid communication with said eluent source, said sample inlet and said input port, and a second communication portion in selective fluid communication with said waste port, said sample outlet and said separator column, said first communication portion and said second communication portion being adapted to cooperate therebetween to load said sample retaining device with sample solution from said sample source, and cooperate to flush substantially all of the known volume of sample solution from the sample retaining device with a substantially precise, predetermined volume of eluent from said eluent source, and through said separator column without passing any eluent through said separator column during the flush.

27. The apparatus as defined in claim 26 wherein,
said first communication portion being selectively movable between a retainer loading position, coupling said sample inlet with said input port to load said retaining device with said sample solution, and a column loading position, coupling said eluent source with said sample inlet to move a fraction of the known volume of sample solution from said retaining device toward said second communication portion; and said second communication portion being selectively movable between a retainer loading condition, coupling said sample outlet with said waste port to load said retaining device with said sample solution when said first communication portion is in said retainer loading position, and a column loading condition, coupling said sample outlet with said separator column to move said fraction of said known volume of sample solution from said retaining and said second communication portion to said separator column when said first communication portion is in said column loading position.

28. The apparatus as defined in claim 26 further including:

a bypass conduit selectively coupling said eluent source with said separator column in a manner bypassing said retaining device to enable chromatographic separation.

29. The apparatus as defined in claim 28 wherein, said bypass conduit is coupled between said first communication portion and said second communication portion, said first communication portion further selectively movable to a bypass position fluid communicating said eluent from said eluent source with said second communication portion while said first communication portion is out of said column loading position, and said second communication portion further selectively movable to a bypass condition fluid communicating said eluent from said eluent source with said separator column while said second communication portion is out of said column loading condition and said first communication portion is in said bypass position.

30. The apparatus as defined in claim 26 wherein, said eluent source includes a high precision eluent pump assembly delivering eluent to said sample retaining device at a substantially constant rate.

31. The apparatus as defined in claim 26 wherein, said first communication portion and said second communication portion cooperate to flush up to about 98% of the known volume of sample solution from the sample retaining device.

32. A method for chromatographic separation and quantitative analysis of ionic species in a sample solution comprising the steps of:

(A) loading sample solution, having trace ionic contaminants, through a sample inlet of a known volume sample retaining device substantially filling said retaining device with said sample solution and removing any non-sample solutions through a sample outlet thereof; and (B) cooperating a first valve portion, selectively fluid communicating a pressurized eluent with the sample inlet, with a second valve portion, selectively fluid communicating said sample outlet with a separator column, to flush substantially all of the known volume of sample solution from the sample retaining device with a substantially precise, predetermined volume of eluent from an eluent source, and through said separator column without passing any eluent through said separator column during the flush.

33. The method as defined in claim 32 further including the step of:

(C) repeating steps A and B, sequentially, until a total predetermined volume of sample solution has passed through said separator column.

34. The method as defined in claim 32 further including the step of:

(D) passing eluent through said ion exchange resin column to separate predetermined ionic contaminants of interest from said separator column.

35. The method as defined in claim 32 wherein, said loading step (A) includes the step of (E) providing fluid coupling of sample solution from a sample source with a sample inlet into said retaining device to enable flow said sample solution therethrough and into said retaining device.

36. The method as defined in claim 35 wherein, said loading step (A) further includes the step of (F) blocking fluid coupling of said eluent with said sample inlet to preclude flow of said eluent therethrough and into said retaining device.

37. The method as defined in claim 36 wherein, said providing step (E) and said blocking step (F) are accomplished by an injection assembly including said first valve portion in selective fluid valve with said eluent source, said sample inlet of retaining device and said sample input port of said sample source, said first valve portion being movable from a column loading position to a retainer loading position, fluid coupling said sample inlet with said sample input port while disconnecting fluid coupling of said eluent through said sample inlet.

38. The method as defined in claim 37 wherein, said loading step (A) is further accomplished by said injection assembly further including said second valve portion in selective fluid valve with a sample waste port of said sample source, said sample outlet of said retaining device and said separator column, said second valve portion being selectively movable from a column loading condition to a retainer loading condition, fluid coupling said sample outlet with said sample waste port while disconnecting fluid coupling of said sample outlet with said separator column, when said first valve portion is in said loop loading position.

\* \* \* \* \*